US006258587B1

(12) United States Patent
Delley et al.

(10) Patent No.: US 6,258,587 B1
(45) Date of Patent: *Jul. 10, 2001

(54) **RECOMBINANT, SEQUENCE-MODIFIED *L. JOHNSONII* BACTERIA WHICH PRODUCE ONLY L(+)-LACTATE**

(75) Inventors: Michèle Delley, Lausanne; Jacques Edouard Germond, Crissier; Luciane Lapierre, Attalens; Beat Mollet; Raymond David Pridmore, both of Lausanne, all of (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/490,217

(22) Filed: Jan. 24, 2000

Related U.S. Application Data

(63) Continuation of application No. 09/070,980, filed on May 1, 1998, now Pat. No. 6,110,725.

(30) Foreign Application Priority Data

May 3, 1997  (EP) .................................................. 97201337

(51) Int. Cl.$^7$ ..................................................... C12N 1/12

(52) U.S. Cl. ................................... 435/252.3; 435/252.9

(58) Field of Search ............................... 435/252.3, 252.9

(56) References Cited

U.S. PATENT DOCUMENTS

| 5,416,020 | 5/1995 | Severson et al. | 435/252.9 |
|---|---|---|---|
| 5,545,554 | 8/1996 | Germond et al. | 435/252.9 |
| 5,603,930 | 2/1997 | Brassart et al. | 424/93.45 |
| 5,747,310 | 5/1998 | Sasaki et al. | 435/172.3 |
| 6,110,725 | * 8/2000 | Delley et al. | 435/252.3 |

FOREIGN PATENT DOCUMENTS 2618692   4/1993  (AU).

OTHER PUBLICATIONS

Horton, "PCR–Mediated Recombination and Mutagenesis," Molecular Biotechnology, vol. 3, 1995, pp. 93–99.
Arrigoni, et al., "Tolerance and absorption of lactose from milk and yogurt during short–bowel syndrome in humans," Am. J. Clin. Nutr. 1994; 60: 926–9.
Bhowmik, et al., "Cloning characterization and insertional inactivation of the *Lactobaccillus helveticus* D(−) lactate dehydrogenase gene", Appl. Microbiol. Biotechnol. (1994) 41: 432–439.
Taguchi et al., "Essential Role of Arginine 235 in the Substrate–Binding of *Lactobacillus plantarum* D–Lactate Dehydrogenase", J. Biochem. 115, 930–936 (1994).
Ferrain, et al., "*Lactobacillus plantarum* LdhL Gene: Overexpression and Deletion", Journal of Bacteriology, vol. 176, No. 3, Feb. 1994 pp. 596–601.

Delcour, et al., "Génétique moléculaire des lactate–déshydrogénases des bactéries lactiques" (Molecular genetics of lactate dehydrogenases from lactic acid bacteria), Lait (1993) 73, 127–131.
Mollet, et al., "Directed Genomic Integration Gene Replacement, and Integrative Gene Expression in *Streptococcus thermophilus*,"Journal of Bacteriology, vol. 175, No. 14, Jul. 1993, pp. 4315–4324.
Kochhar, et al., "Primary Structure, Physicochemical Properties, and Chemical Modification of NAD$^+$–dependent D–Lactate Dehydrogenase: Evidence for the Presence of ARG–235, HIS–303, TYR–101, and TRP–19 at or Near the Active Site," The Journal of Biological Chemistry, vol. 267, No. 12, Issue of Apr. 25, pp. 8499–8513, 1992.
Bernard, et al., "Cloning of the D–lactate dehydrogenase gene from *Lactobacillus delbrueckii* subsp. *bulgaricus* by complementation in *Escherichia coli*", FEBS Letters, vol. 290, No. 1, 2, 61–64, Sep. 1991.
Taguchi, et al., "D–lactate Dehydrogenase Is a Member of the D–Isomer–specific 2 Hydroxyacid Dehydrogenase Family", The Journal of Biological Chemistry, vol. 266, No. 19, Issue of Jul. 15, pp. 12588–12594, 1991.
Marteau, et al., "Effect of the microbial lactase (EC 3.2.1.23) activity in yoghurt on the intestinal absorption of lactose: an in vivo study in lactase–deficient humans," British Journal of Nutrition (1990), 64, 71–79.
Delley, et al., "DNA Probe for *Lactobacillus delbrueckii*," Applied and Environmental Microbiology, vol. 56, No. 6, Jun. 1990, pp. 1967–1970.
Takemoto, et al., "A New Method for Conjugal Transfer of Plasmid pAMB1 to *Lactobacillus plantarum* Using Polyethylene Glycol," Agric. Biol. Chem., 53 (12), 3333–3334 1989.
Sambrook, et al., "Molecular Cloning: A Laboratory Manual," Cold Spring Harbor Laboratory Press, Second Edition, pp. 1.25–1.28, 1.38–1.39, 4.33–4.34, 4.37–4.38, 16.30–16.31, 16.54–16.55 (1989).
Kolars, et al., "Yoghurt—An Autodigesting Source of Lactose," The New England Journal of Medicine, vol. 310, No. 1, pp. 1–3, Jan. 5, 1984.
Gasson, "Plasmid Complements of *Streptococcus lactis* NCDO 712 and Other Lactic Streptococci After Protoplast–Induced Curing," Journal of Bacteriology, vol. 154, No. 1, Apr. 1983, pp. 1–9.

(List continued on next page.)

*Primary Examiner*—Ponnathapu Achutamurthy
*Assistant Examiner*—Peter P. Tung
(74) *Attorney, Agent, or Firm*—Vogt & O'Donnell, LLP (57) ABSTRACT

Recombinant strains of *L. johnsonii* which have capacities of surviving passage through the intestine, adhering to human intestinal cells and increasing phagocytosis of macrophages and which have a sequence of gene coding which is an *L. johnsonii* strain sequence of gene coding for D–lactate dehydrogenase modified so that the recombinant strain produces only L(+)-lactate.

2 Claims, 4 Drawing Sheets

OTHER PUBLICATIONS

Clewell, et al., "Characterization of Three Plasmid Deoxyribonucleic Acid Molecules in a Strain of *Streptococcus faecalis*: Identification of a Plasmid Determining Erythromycin Resistance", Journal of Bacteriology, vol. 117, No. 1, Jan. 1974, pp. 283–289.

Efthymieu, et al., "An Antigenic Analysis of *Lactobacillus acidopholus*," The Journal of Infectious Diseases, vol. 110, 1962, pp. 258–267.

* cited by examiner

RECOMBINANT, SEQUENCE-MODIFIED *L. JOHNSONII* BACTERIA WHICH PRODUCE ONLY L(+)-LACTATE

CROSS REFERENCE TO RELATED APPLICATION

This is a continuing application of application Ser. No. 09/070,980 which was filed May 1, 1998 and which is issued U.S. Pat. No. 6,110,725.

BACKGROUND OF THE INVENTION

The present invention relates to bacteria strains which produce lactate and to *L. johnsonii* strains and further to recombinant, i.e., genetically modified/bacteria strains.

Fermentation is a degradation of a carbon source during which the final hydrogen acceptor is an organic compound. By way of lactic acid fermentation, certain bacterial strains produce a racemic mixture of the two isomeric forms of lactate, D(−)-lactate and L(+)-lactate, for the regeneration of $NAD^+$, by the reduction of pyruvate by means of two specific NAD-dependent lactate dehydrogenases.

Some individuals are known to exhibit an intolerance to the reduction of lactose. This poor digestion of lactose is often due to the absence of a sufficient amount of β-galactosidase in the small intestine. Various studies (Kolars et al., N. Engl. J. Med., 310, 1–3, 1984; Marteau et al., Br. J. Nutr., 64, 71–79, 1990; and Arrigoni et al., Am. J. Clin. Nutr., 60, 926–929, 1994) have demonstrated the fact that these people digest and tolerate the lactose contained in yoghurts better than that contained in milk. This better digestion and better lactose tolerance are due especially to the activity of the β-galactosidase of the bacteria contained in yoghurts during intestinal transit.

It is further known that D(−)-lactate can give rise to acidosis problems in children. For these reasons, the World Health Organization (FAO/WHO, 1967; 1974) recommends that D(−)-lactate should not be added to children's food, either on its own or as a racemic mixture with L(+)-lactate. Also, the daily consumption limit of D(−)-lactate for adults preferably does not exceed 100 mg/kg of the human body.

Bacterial strains which have been genetically recombined so as to produce only L(+)-lactate are now known.

T. Bhowmik et al. (Appl. Microbiol. Biotechnol., 432–439, 1994) describe a technique for the isolation and inactivation, by directed mutagenesis, of the gene coding for the enzyme D-lactate dehydrogenase of the strain *Lactobacillus helveticus* CNRZ32, particularly the strain *Lactobacillus helveticus* CNRZ32(pSUW104), which produces only L(+)-lactate. This strain is obtained by the electroporation of integrating vector pSUW104, which comprises vector pSA3 and the 0.6 kb SalI-SphI internal fragment of the gene coding for the enzyme D-lactate dehydrogenase of *Lactobacillus helveticus*.

However, bacterial strains with the capacity to survive in the intestine, adhere to intestinal cells and effect immunomodulation, which have been genetically recombined so as to produce only L(+)-lactate, are not known at the present time. Now, it would be very valuable, for the preparation of food products, to have such bacterial strains with the capacity to survive in the intestinal tract, which possess these beneficial properties on human health and produce only L(+)-lactate, so as to avoid the adverse effects due to D(−)-lactate.

The object of the present invention is to meet these needs.

SUMMARY OF THE INVENTION

The present invention provides recombinant bacterial strains wherein the strains are modified genetically to produce only L(+)-lactate and which have the capacity to survive in the intestine, adhere to human intestinal cells and effect The present invention relates especially to bacterial strains in which the gene coding for the enzyme D-lactate dehydrogenase is inactivated.

The present invention relates especially to strains of *Lactobacillus acidophilus, Lactobacillus johnsonii, Lactobacillus gasseri, Lactobacillus crispatus, Lactobacillus amylovorus* or *Lactobacillus gallinarum*.

The present invention further relates to the strain CNCM I-1851 and the strain CNCM I-1852.

A further subject of the present invention is a method of producing a bacterial strain which has been genetically recombined so as to produce only L(+)-lactate.

Finally, the present invention relates to the use of bacterial strains, obtained by carrying out the method according to the present invention for the preparation of food products.

DETAILED DESCRIPTION OF THE INVENTION

In this description, the expression "conjugative vector" is used to denote a DNA vector transferable by conjugation between two strains of different species of lactic acid bacteria.

Also, in this description, the expression "strain with the capacity to survive in the intestine" is used to denote a lactic acid bacterial strain which, after consumption, is found in the stool.

Finally, in this description, the expression "bacterial strain with the capacity to effect immunomodulation" is used to denote a lactic acid bacterial strain which has a beneficial effect on the immune system, especially the property of increasing the phagocytosis of the macrophages.

The present invention therefore relates to bacterial strains with the capacity to survive in the intestine, adhere to human intestinal cells and effect immunomodulation, which has been genetically recombined so as to produce only L(+)-lactate.

The present invention relates especially to bacterial strains with the capacity to survive in the intestine, adhere to human intestinal cells and effect immunomodulation, in which the gene coding for the enzyme D-lactate dehydrogenase has been inactivated.

The strains according to the present invention can be a strain of *Lactobacillus acidophilus, Lactobacillus johnsonii, Lactobaclllus gasseri, Lactobacillus crispatus, Lactobacillus amylovorus* or *Lactobacillus gallinarum*, for example.

Two strains of *Lactobacillus johnsonii* which have been genetically recombined so as to produce only L(+)-lactate have been isolated in particular. These strains were deposited on Feb. 20, 1997, under the terms of the Budapest Treaty, in the Collection Nationale de Cultures de Microorganismes, INSTITUT PASTEUR, 25, rue du Docteur Roux, F-75724 PARIS CIDEX 15, where they were aven the deposit number CNCM I-1851 and the deposit number CNCM I-1852 respectively.

The present invention further relates to a method of preparing such a strain, wherein the sequence of the gene coding for the enzyme D-lactate dehydrogenase is isolated from a host bacterial strain with the capacity to survive in the intestine, adhere to human intestinal cells and effect immunomodulation, a directed mutagenesis is carried out on this sequence to give a modified sequence, this modified sequence is integrated into a conjugative vector, the conjugative vector is transferred by conjugation into the host bacterial strain, and then the host bacteria in which the sequence coding for the enzyme D-lactate dehydrogenase has been replaced by homologous recombination with the modified sequence are selected.

In the method according to the present invention, the sequence of the gene coding for the enzyme D-lactate dehydrogenase can be isolated from the host bacterial strain by PCR, by cloning or by complementation, for example.

A directed mutagenesis can be carried out on this sequence to give a modified sequence by the Gene Splicing Overlap Extension method (Molecular Biotechnology, R. M. Horton, 1995, 3, 93–99), which consists in generating a gene sequence in which one or more nucleotides, for example, are introduced or deleted.

To integrate the modified sequence into a conjugative vector of a donor bacterial strain of the host bacterial strain, a donor bacterial strain containing a conjugative vector which does not have the capacity to replicate in the host bacterial strain can be selected, a construction can be produced by ligation of the modified sequence into a first vector which is incapable of multiplying in the donor bacterial strain of the host bacterium, this construction can be introduced into the donor bacterial strain, and then the donor bacteria in which the first vector and the conjugative vector have recombined, for example, can be selected.

The conjugative vector containing the modified sequence is therefore transferred by conjugation into the host bacterial strain.

The host bacteria in which the sequence coding for the enzyme D-lactate dehydrogenase has been replaced by homologous recombination with the modified sequence are then selected.

The host bacteria which have integrated the conjugative vector into their genome, for example, can be selected on a medium containing certain antibiotics. In fact, through the integration of the conjugative vector into their genome, these bacteria can express the antibiotic resistance genes contained in the sequence of said vector.

Finally, the host bacteria in which the DNA sequences of the conjugative vector have been removed from the genome, with the exception of the modified sequence, are selected.

This can be done by carrying out a first selection on a medium containing antibiotics so as to select the bacteria sensitive to these antibiotics, i.e. the wild-type bacteria and the genetically transformed bacteria now containing only the fragment of the modified sequence of the gene, for example.

An enzymatic colour test can then be performed in the presence of D-lactate dehydrogenase, tetrazolium salt and diaphorase so as to differentiate the wild-type bacteria from the genetically transformed bacteria according to :he present invention, for example. This enzymatic test makes it possible to demonstrate the fact that the bacteria which do not produce D(−)-lactate cannot oxidize D(−)-lactate when the enzyme D-lactate dehydrogenase is added to the medium; consequently, the tetrazolium salt in the medium is not educed by the enzyme diaphorase, in the absence of oxidized D-lactate, and these bacteria remain colourless.

A PCR can then be carried out on the genomic sequences of the genetically recombined host bacterium according to the present invention using primers specific for the host bacterial strain, the PCR product can then be digested in the presence of specific restriction enzymes, and the size of fragments generated in this way can be compared with those obtained, after digestion with these same restriction enzymes, from the genome of a wild-type host bacterium, for example The method of preparing the bacterial strains according to the present invention, and these genetically recombined bacterial strains, are characterized in greater detail below by means of biochemical and molecular analyzes, with reference to the accompanying drawing figures.

DETAILED DESCRIPTION OF THE DRAWING FIGURES

DETAILED DESCRIPTION OF THE INVENTION WITH REFERENCE TO THE DRAWING FIGURES

I. Isolation of the Sequence of the Gene Coding for the Enzyme D-lactate Dehydrogenase of *Lactobacillus johnsonii* La1

*Lactobacillus johnsonii* La1 is grown on an MRS medium overnight at 37° C. The culture is then transferred to a tube containing an MRS medium and allowed to grow to an $OD_{600}$ of about 1.

The genome of *Lactobacillus johnsonii* La1 is isolated by the method described in the article "DNA probe for *Lactobacillus delbrueckii*" (B. Mollet et al., Applied and Environmental Microbiology, June 1990, vol. 56(6), p. 967–1970).

The sequence of the gene coding for the enzyme D-lactate dehydrogenase of *Lactobacius johnsonii* La1 is then isolated by PCR using as specific primers the sequences SEQ ID NO:1 and SEQ ID NO:2 described below, which are sequences of conserved regions of the gene coding for the enzyme D-lactate dehydrogenase of *Lactobacillus helveticus* (Eur. J. Biochem., Cloning and overexpression of *Lactobacillus helveticus* D-lactate dehydrogenase gene in *Escherichia coli*, Kochhar et al., 208, 799–805, 1992).

This gives an 890 bp fragment, which is cloned into vector pGEMT marketed by Promega, MADISON, Wiss.—USA, and then sequenced. To isolate the complete sequence of the gene coding for the enzyme D-lactate dehydrogenase of *Lactobacillus johnsonii* La1, a Southern blot is then effected with different restriction enzymes, the probe used being the sequence previously obtained by PCR.

A 3 kb nucleotide sequence comprising two open reading frames of opposite orientation is isolated in this way.

A high degree of homology is found between one of the open reading frames and the sequence of the gene coding for the enzyme D-lactate dehydrogenase of *Lactobacillus helveticus*. The sequence of this open reading frame has a length of 1014 nucleotides and has a homology of 85% with the sequence of the gene coding for the enzyme D-lactate dehydrogenase of *Lactobacillus helveticus* and a homology of 81% with that of *Lactobacillus bulgaricus* (FEBS Lett., Bernard et al., 1991, 290, 61–64). This sequence codes for a polypertide of 338 amino acids.

II. Directed Mutagenesis on the Sequence Coding for the Enzyme D-lactate Dehydrogenase of *Lactobacillus johnsonii* La1

A directed mutagenesis is carried out on the isolated sequence by the Gene splicing Overlap Extension method (Molecular Biotechnology, R. M. Horton, 1995, 3, 93–99). This sequence is subjected by PCR to a deletion of 11 nucleotides and an insertion of 3 nucleotides at -he centre. These sequence modifications have the effect of creating a DraI restriction site and eliminating an EcoRV restriction site. These two restriction site modifications are used as a marker to demonstrate the presence of the modified sequence of the gene coding for the D-lactate dehydrogenase of *Lactobacillus johnsonii* La1 in the different vectors used in the remainder of the construction, and in the selection of the mutants which have integrated only the modified sequence of the gene coding for the enzyme D-lactate dehydrogenase.

The gene sequence modified in this way codes for a polypeptide of 181 amino acids instead of a polypeptide of 338 amino acids.

III. Cloning of the Modified Sequence of the Gene Coding for the Enzyme D-lactate Dehydrogenase of *Lactobacillus johnsonii* La1 into Vector pGEMT of *Escherichia coli*

The modified sequence of the gene coding for the enzyme D-lactate dehydrogenase is cloned into vector pGEMT of *Escherichia coli*.

This is done by ligating the modified sequence of the gene into this vector pGEMT containing the ampicillin resistance gene.

Figure 1:
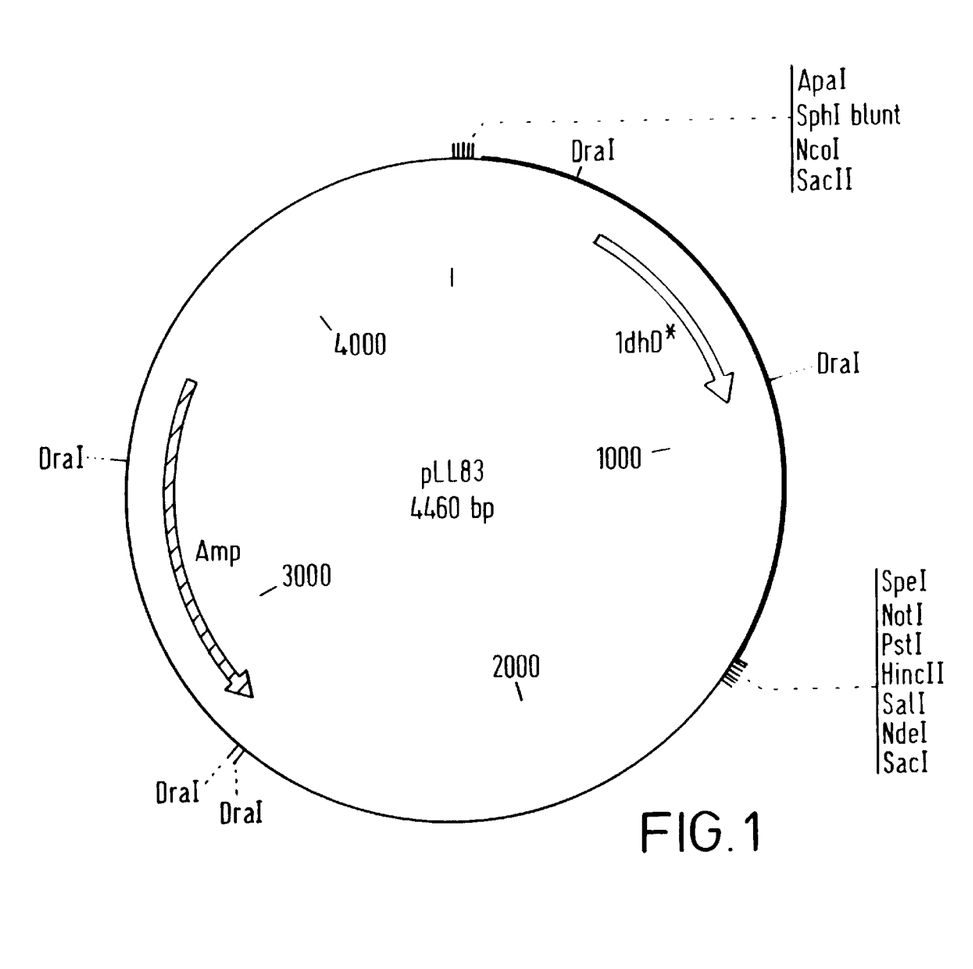
FIG. 1 shows vector pLL83, which is the ligation product of vector pGEMT, marketed by Promega, MADISON, Wiss.—USA, and the modified sequence of he gene coding for the enzyme D-lactate dehydrogenase.

This ligation mixture is then introduced into *Escherichia coil* XL1-Blue by electroporation and the positive clones are selected in the presence of X-gal and IPTG (Sambrook et al., molecular cloning: a laboratory manual, 2nd ed., 1989). The resulting vector, as shown in FIG. 1, is called pLL83.

Vector pLL83 is then purified by the method of alkaline lysis (Sambrook et al., Molecular cloning: a laboratory manual, 2nd ed., 1989).

The fragment comprising the modified sequence of the gene coding for the enzyme D-lactate dehydrogenase is then isolated from vector pLL83 purified in this way. This is done by carrying out a digestion with the restriction enzyme SphI at the SphI restriction site on vector pLL83. The enzyme T4 polymerase is then reacted at this cleavage so as to add nucleotides and obtain a blunt cut. Finally, a digestion is carried out with the restriction enzyme SpeI.

In a parallel operation, a digestion is carried out on a vector which is incapable of replicating in the donor bacterial strain, *Lactococcus lactis*, and in the host bacterial strain, *Lactobacillus johnsonii*. This digestion is carried out at a restriction site, after which the enzyme T4 polymerase is reacted at this cleavage so as to add nucleotides and obtain a blunt cut. Finally, a digestion is carried out with the restriction enzyme SpeI. Vector pMD14, described in FIG. 2, can be used in particular for producing this construction. It is possible to carry out a digestion on this vector pMD14 with the restriction enzyme EcoRI, then react the enzyme T4 polymerase and finally carry out a digestion with the restriction enzyme SpeI.

Figure 2:
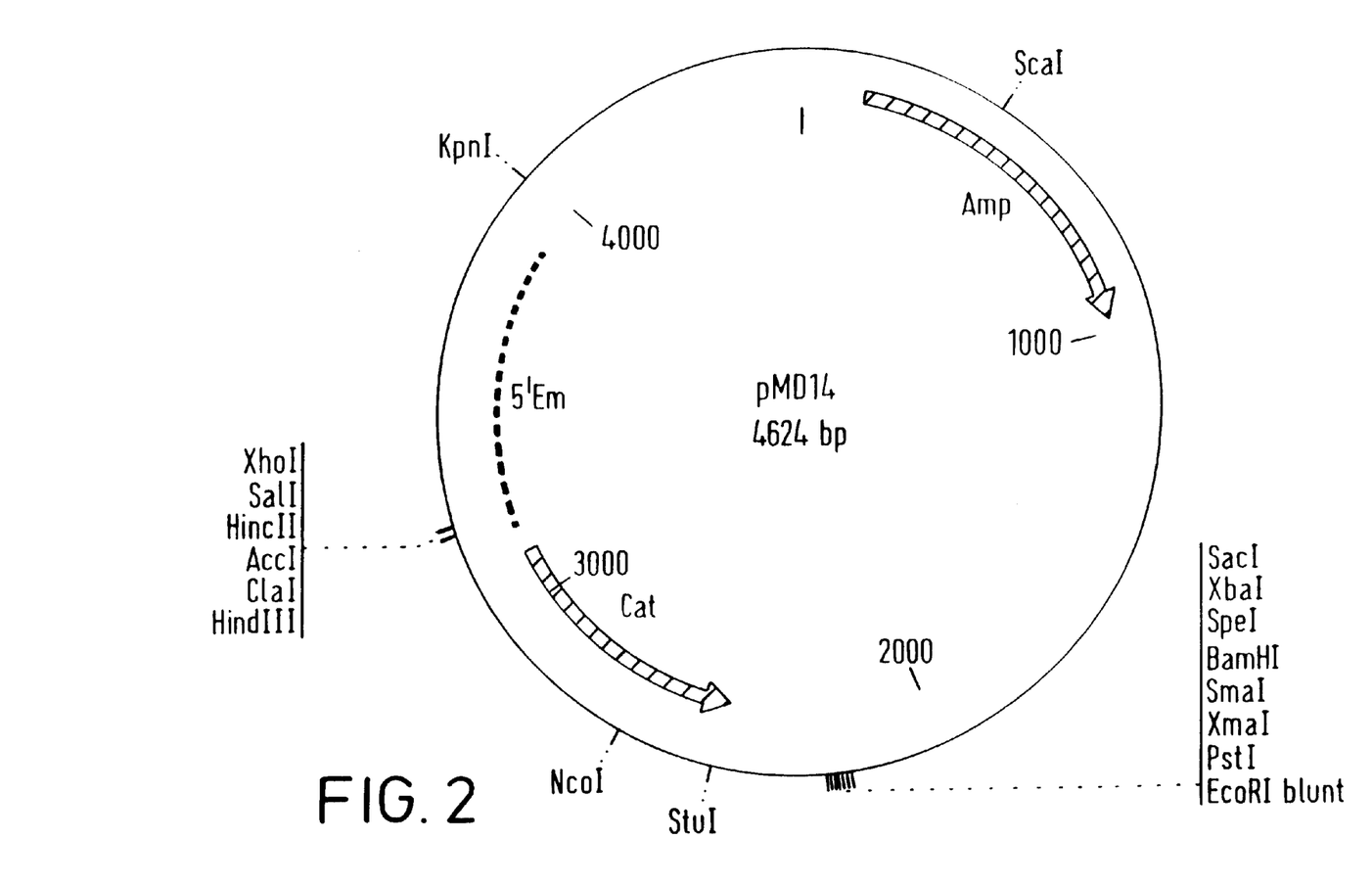
FIG. 2 shows vector pMD14, which is constructed from vector pBlueScript SK+ of *Eschericha coli* (Stratagene, LA YOLLA, Calif.—USA) and which contains the chloramphenicol (cat) resistance gene of vector pNZ12 (Gasson et al., J. Bacteriol., 154, 1–9, 1983) and the 5' region upstream of the sequence of the erythromycin resistance gene of vector pAMβ1 (Clewell et al., J. Bacteriol., 33, 426–428, 1974), which was isolated from plasmid pUC-838 (Mallet et al., J. Bacteriol., 175, 4315–4324, 1993).

The fragment of vector pLL83 comprising the modified sequence of the gene coding for the enzyme D-lactate dehydrogenase is then introduced into vector pMD14.

The ligation mixture is then introduced into *Escherichia coli* XL1-Blue by electroporation.

About one hundred colonies of *Escherichia coli* XL1-Blue constructed in this way are then deposited on microfiltration plates, they are then transferred to a nitrocellulose membrane, they are then lyzed in situ and a hybridization is performed with an internal fragment of the gene coding for the enzyme D-lactate dehydrogenase of *Lactobacillus johnsonii* La1.

Figure 3:
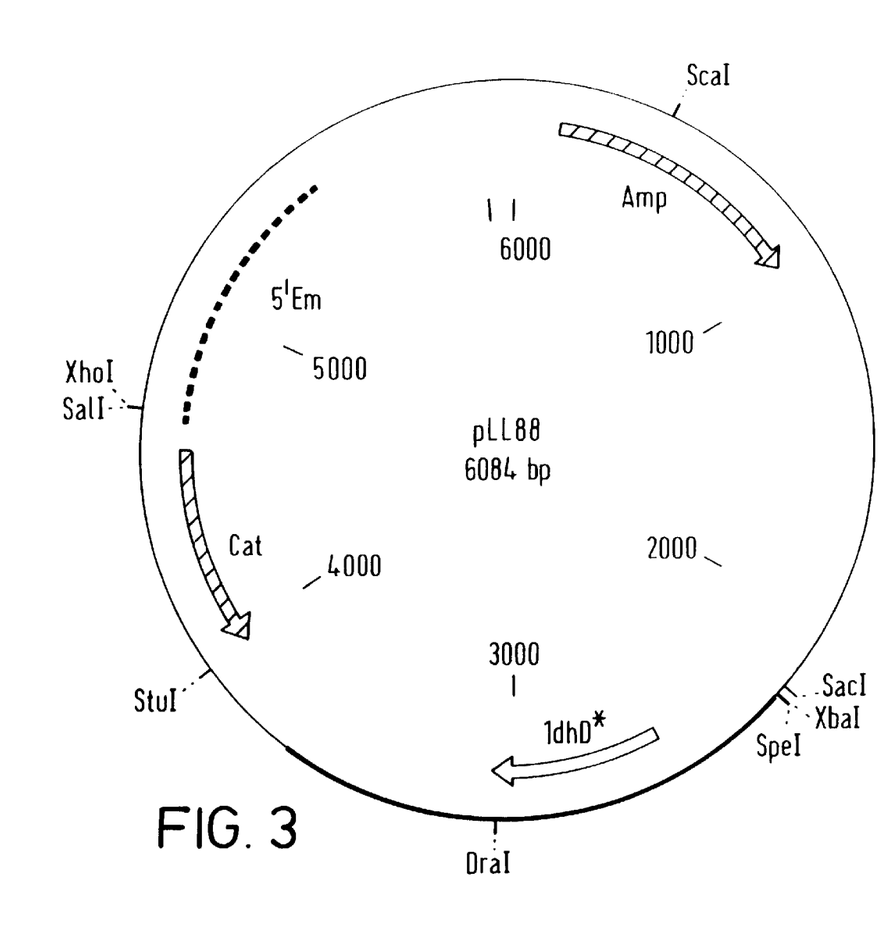
FIG. 3 shows vector pLL88, which is the ligation product of the fragment of vector pLL83 comprising the modified sequence of the gene coding for the enzyme D-lactate dehydrogenase, in vector pMD14.

3 positive clones containing vector pLL88, described in FIG. 3, are thus selected. The sequencing of vector pLL88 demonstrates the fact that it comprises the modified sequence of the gene coding for the enzyme D-lactate dehydrogenase of *Lactobacillus johnsonii* Lap1, the regions of pGEMT flanking this sequence, and vector pMD14.

IV. Introduction of Vector pLL88 into the Strain *Lactococcus lactis* MG1363(pAMβ1)

Vector pLL88 is introduced into the strain *Lactococcus lactis* MG1363(pAMβ1) by electroporation.

Figure 4:
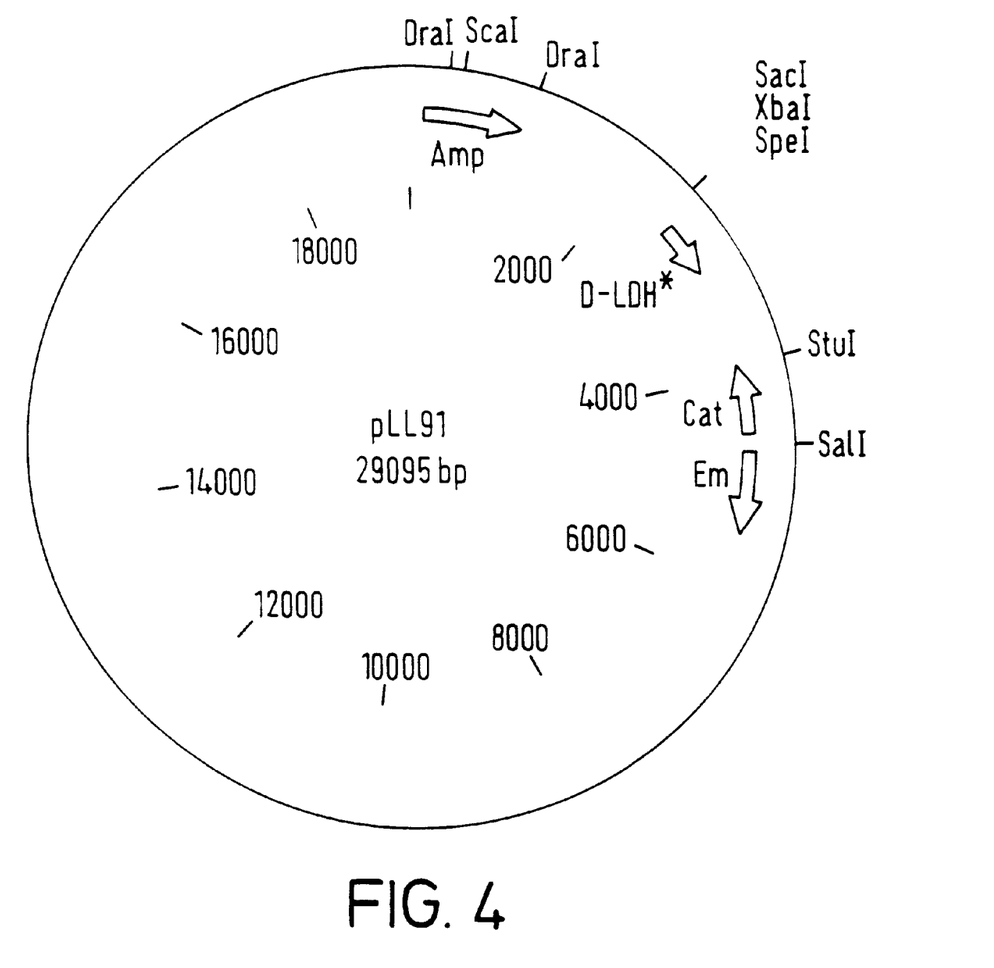
FIG. 4 shows vector pLL91, which comprises the sequence of vector pLL88 and that of vector pAMβ1 (Clewell et al., J. Bacteriol., 33, 426–428, 1974).

The transformants thus produced are then placed on a GM17 agar medium containing 12 μ/ml of chloramphenicol and incubated at 30° C. overnight. Vector pLL88 cannot replicate in Gram-positive bacteria. All the *Lactococcus lactis* MG1363(pAMβ1) bacteria which have integrated, by homologous region, vector pLL88 comprising the chloramphenicol resistance gene into conjugative vector pAMβ1, described in FIG. 5, are thus selected on this medium containing chloramphenicol. This construction, comprising the sequence of vector pLL88 and that of vector pAMβ1, will subsequently be called vector pLL91, described in FIG. 4.

V. Conditions of Conjugation

*Lactococcus lactis* MG1363 containing vector pLL91 is cultivated on a GM17 medium containing 12 μg/ml of chloramphenicol, and *Lactobacillus johnsonii* La1 is cultivated on an MRS medium.

0.2% of the *Lactobacillus johnsonii* La1 culture prepared in this way is inoculated into a tube containing a fresh MRS medium, and the mixture is incubated for 5 h 00 min at 37° C.

The *Lactococcus lactis* MG1363 and *Lactobacillus johnsonii* La1 cultures are then centrifuged at 3000 rpm for 5 min and each residue is transferred to 10 ml of LCMG medium (Efthymiou et al., An antigenic analysis of Lactobacillus acidophilus, J. Infect. Dis., 1962, 110, 258–267) containing 10 g of trypticase, 5 g of yeast extract, 3 g of tryptose, 3 g of $K_2HPO_4$, 3 g of $KH_2PO_4$, 2 g of ammonium citrate, 5 ml of solution enriched in mineral salts, 1 g of Tween 80, 1 g of sodium acetate, 20 g of glucose and 0.2 g of cysteine.

1 ml of culture of the donor strain *Lactococcus lactis* MG1363 prepared in this way is then mixed with 10 ml of culture of the recipient strain *Lactobacillus johnsonii* La1 prepared in this way, and the mixture is centrifuged.

The supernatant is discarded and the concentrated residue is deposited on plates of PEG agar medium (Takemoto et al., Agric. Biol. Chem., 1989, 53, 3333–3334) containing 5 g of PEG6000, 15 g of agar, 1000 ml of sugar-free LCMG solution, 100 ml of sugar-containing solution and 10 ml of mineral salt solution. These plates are left at room temperature until the residue is dry, and it is then covered with 10 ml of LCMG medium containing 7% of agar.

The plates are then incubated overnight at 37° C., the agar containing the bacteria cells which have grown is then cut out and this agar is deposited in tubes containing 10 ml of LCMG medium.

The tubes are then shaken vigorously and the cultures prepared in this way are diluted in TS medium containing 1 g/l of tryptone and 8.5 g/l of NaCl.

The diluted cultures are then deposited on plates of MRS agar medium containing 100 µg/ml of phosphomycin and 14 µg/ml of chloramphenicol, and incubated at 37° C. for 48 h 00 min under anaerobic conditions.

VI. Conjugation and Integration of Vector pLL91 into *Lactobacillus johnsonii* La1

*Lactococcus lactis* MG1363 containing vector pLL91 is conjugated with *Lactobacillus johnsonii* La1. This conjugation has a frequency of between $1 \times 10^{-5}$ and $3 \times 10^{-7}$ transformants/recipient cells.

6 colonies of *Lactobacillus johnsonii* La1 resistant to chloramphenicol and phosphomycin are then selected and cultivated at 37° C. on an MRS medium before being transferred for a few hours at 45° C. so as to select the *Lactobacillus johnsonii* La1 bacteria which have integrated vector pLL91 into their genome, by homologous region, at the sequence coding for the enzyme D-lactate dehydrogenase. In fact, vector pAMβ1 contained in vector pLL91 is incapable of replicating at a temperature above 42° C. Thus all the *Lactobacillus johnsonii* La1 bacteria which are resistant to chloramphenicol and can grow at 45° C. have integrated vector pLL91 into their genome, by homologous region, at the sequence coding for the enzyme D-lactate dehydrogenase.

Therefore the integration of vector pLL91 into the genome of *Lactobacillus johnsonii* La1 is obtained by a single cross-over either at the terminal 5' region of the sequence of the gene coding for D-lactate dehydrogenase, or at the terminal 3' region of the sequence of this gene.

VII. Verification of the Integration of the Modified Sequence of the Gene Coding for the Enzyme D-lactate Dehydrogenase into the Chromosomal DNA of *Lactobacillus johnsonii* La1

The integration of vector pLL91 into the genome of *Lactobacillus johnsonii* La1 is verified by PCR.

This is done using primers specific for the genome of *Lactobacillus johnsonii* La1, whose sequences are the sequences SEQ ID NO:3 and SEQ ID NO:4 described below, and primers specific for vector pLL91, whose sequences are the sequences SEQ ID NO:5 and SEQ ID NO:6 described below. The fragments amplified in this way by PCR are then digested with the restriction enzyme EcoRV, whose restriction site is located in the original sequence of the gene coding for the enzyme D-lactate dehydrogenase, and with the restriction enzyme DraI, whose restriction site is located in the modified sequence of the gene coding for the enzyme D-lactate dehydrogenase, so as to demonstrate the fact that the integration by a single cross-over has taken place at the terminal 5' region or at the terminal 3' region of the original sequence of the gene. A *Lactobacillus johnsonii* La1 bacterium genetically modified by integration of the modified sequence of the gene into the terminal 5' region of the original sequence of the gene, and a *Lactobacillus johnsonii* La1 bacterium genetically modified by integration of the modified sequence of the gene into the terminal 3' region of the original sequence of the gene, are then selected.

The integration of vector pLL91 into the genome of *Lactobacillus johnsonii* La1 is then verified by effecting a Southern blot of the genome of these two genetically modified *Lactobacillus johnsonii* La1 bacteria selected above. This is done by digesting the genomic DNA of these two bacteria with different restriction enzymes whose restriction sites are located in the genome, on vector pLL91 and on the modified sequence of the gene coding for D-lactate dehydrogenase. The hybridization probe used is a fragment of the original sequence of the gene coding for the enzyme D-lactate dehydrogenase.

This demonstrates the fact that the genome fragments of the two genetically modified *Lactobacillus johnsonii* La1 bacteria, obtained after digestion with different restriction enzymes, are of a different size from the fragments obtained after digestion of the genome of the wild-type *Lactobacillus johnsonii* La1 bacterium with these same restriction enzymes.

VIII. Resolution of the Integration

The integration is resolved by releasing vector pLL91 from the genome. The loss of vector pLL91 is obtained either by a single cross-over between the terminal 5' region of the original sequence of the gene coding for the enzyme D-lactate dehydrogenase and that of the modified sequence of said gene, or by a single cross-over between the terminal 3' region of the original sequence of the gene coding for the enzyme D-lactate dehydrogenase and that of the modified sequence of said gene.

The integration is resolved at 37° C., which is a permissive temperature for the vector, so as to favour the release of vector pLL91 from the genome.

An enzymatic colour test is performed in the presence of D-lactate dehydrogenase, tetrazolium salt and diaphorase so as to differentiate the wild-type bacteria from the genetically transformed bacteria according to the present invention. This enzymatic test makes it possible to demonstrate the fact that the bacteria which do not produce D(−)-lactate cannot oxidize D(−)-lactate when the enzyme D-lactate dehydrogenase is added to the medium; consequently, the tetrazolium salt in the medium is not reduced by the enzyme diaphorase, in the absence of oxidized D-lactate, and these bacteria remain colourless.

EXAMPLES

The Examples below are given in order to illustrate the use of a bacterial strain according to the present invention in the manufacture of food products. The percentages are given by weight, unless indicated otherwise.

Example 1

Yoghurts are prepared from the strain *Lactobacillus johnsonii* CNCM I-1851 obtained by carrying out the method according to the present invention.

This is done by preparing 500 ml of 9% reconstituted skimmed milk powder, adding 0.1% of yeast extract and sterilizing the mixture in an autoclave for 15 min at 121° C. It is then left to cool to 40° C. before the incorporation of 10% by volume of an active culture of the strain *Lactobacillus johnsonii* CNCM I-1851, containing $5.10^8$ microorganisms/cm$^3$.

This preparation is incubated for 4 h 00 min at 40° C. to produce a leaven containing about $2.5.10^8$ microorganisms/cm$^3$.

In a parallel operation, a leaven containing about $5.10^8$ thickening *Streptococcus thermophilus* bacteria/cm$^3$ is prepared by the method described above.

A mixture containing 1.5% of fat and 3% of skimmed milk powder is pasteurized at 90° C. for 30 min. 1% of *Lactobacillus johnsonii* CNCM I-1851 leaven and 3% of *Streptococcus thermophilus* leaven are then added Go this mixture.

This preparation is then mixed and incubated for 4 h 20 min at 40° C. to give a preparation of pH 4.6.

This gives yoghurts of pleasant texture in which the concentration of *Lactobacillus johnsonii* CNCM I-1851 is $1 \times 10^8$ cells/cm$^3$ and the concentration of *Streptococcus thermophilus* is $1 \times 10^8$ cells/cm$^3$.

Example 2

The procedure is as described in Example 1 except that the yoghurts produced are diluted to 50% with sterile distilled water so that this preparation can be used in parenteral nutrition in a hospital environment.

Example 3

A fermented milk is prepared from the strain *Lactobacillus johnsonii* CNCM I-1852 obtained by carrying out the method according to the present invention.

This is done by heating 1 l of milk at 120° C. for 15 min in order to denature it.

It is then cooled to 37° C. and inoculated with 5% v/v of *Lactobacillus johnsonii* CNCM I-1852 obtained by carrying out the method according to the present invention.

The preparation produced in this way is incubated at room temperature for 18 to 24 h until its acidity level reaches a value of 1%.

Finally, the fermented milk produced is bottled and stored chilled.

Example 4

A fromage frais is prepared from the strain *Lactobacillus johnsonii* CNCM I-1852 obtained by carrying out the method according to the present invention.

This is done by heating 1 l of milk at 72° C. for 15 min and then leaving it to cool to 19° C.

It is then inoculated with 0.5% v/v of a mixture of bacteria containing a *Lactococcus lactis cremoris*, a *Lactococcus lactis diacetylactis* and the strain *Lactobacillus johnsonii* CNCM I-1852.

The resulting mixture is incubated at about 20° C. until the pH of the milk is 4.6.

The milk coagulated in this way is then poured into nylon bags so as to drain off the excess water contained in the fromage frais produced.

The fromage frais is then mixed with. an antimycotic agent, such as potassium sorbate, to orevent mould.

Finally, it is homogenized by slow mixing to give a fromage frais of smooth texture.

The fromage frais produced by this process is packaged in small jars, which can be stored at 4–5° C. for 4 to 5 weeks.

What is claimed is:

1. A recombinant strain of *L. johnsonii* which has capacities which comprise surviving passage through the intestine, adhering to human intestinal cells and increasing the phagocytosis of macrophages and wherein the recombinant strain comprises a DNA sequence coding for D-lactate dehydrogenase which is modified so that the recombinant strain produces only L(+)-lactate.

2. A recombinant strain according to claim 1 wherein the modified sequence lacks a DNA coding sequence for D-lactate dehydrogenase.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

GCTTACGCTA TTCGAAAAGA CG                                 22

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

```
                                              -continued

GTAGTGTAGA AGGCGGTGTG TGG                                                   23

(2) INFORMATION FOR SEQ ID NO:3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

TGGTTGCCAA GTATTAG                                                          17

(2) INFORMATION FOR SEQ ID NO:4:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:

GCTAAGTCAT TAGTGCC                                                          17

(2) INFORMATION FOR SEQ ID NO:5:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

ACAAAAGCTG GAGCTCC                                                          17

(2) INFORMATION FOR SEQ ID NO:6:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:6:

TTGACGTTGA GCCTCGG                                                          17
```